United States Patent
Puiseux et al.

(10) Patent No.: US 12,405,336 B2
(45) Date of Patent: Sep. 2, 2025

(54) CHARACTERIZATION OF DISTORTIONS IN MAGNETIC RESONANCE IMAGING

(71) Applicants: Alara Expertise, Entzheim (FR); Spin Up, Entzheim (FR)

(72) Inventors: Thomas Puiseux, Toulouse (FR); Anou Sewonu, Saint-Herblain (FR); Ramiro Moreno, Toulouse (FR)

(73) Assignees: Alara Expertise, Entzheim (FR); Spin Up, Entzheim (FR)

( * ) Notice: Subject to any disclaimer, the term of this patent is extended or adjusted under 35 U.S.C. 154(b) by 69 days.

(21) Appl. No.: 18/255,822

(22) PCT Filed: Dec. 1, 2021

(86) PCT No.: PCT/FR2021/052173
§ 371 (c)(1),
(2) Date: Jun. 2, 2023

(87) PCT Pub. No.: WO2022/117957
PCT Pub. Date: Jun. 9, 2022

(65) Prior Publication Data
US 2024/0012081 A1    Jan. 11, 2024

(30) Foreign Application Priority Data
Dec. 2, 2020 (FR) .................................. 2012544

(51) Int. Cl.
*G01R 33/58* (2006.01)
*A61B 6/58* (2024.01)
*G01R 33/563* (2006.01)

(52) U.S. Cl.
CPC .............. *G01R 33/58* (2013.01); *A61B 6/583* (2013.01); *G01R 33/56308* (2013.01)

(58) Field of Classification Search
CPC .......... G01R 33/5608; G01R 33/56308; G01R 33/56341; G01R 33/56366; G01R 33/58; G01R 33/583; A61B 6/583
See application file for complete search history.

(56) References Cited

U.S. PATENT DOCUMENTS

2019/0033419 A1* 1/2019 Golay .................... G01R 33/30
2023/0222708 A1* 7/2023 Christodoulou ... G01R 33/5608
  324/309

FOREIGN PATENT DOCUMENTS

WO    2019/211556 A1    11/2019

OTHER PUBLICATIONS

[Online] "Realization of a Flow Phantom for Quality Control in MRI", Report of the ABIH2012 Content Training Course, 2012, Accessed Jun. 2, 2023, (Available at https://www.utc.fr/tsibh/public/3abih/12/stage/litov/index.html), 26 pages.

(Continued)

*Primary Examiner* — Steven L Yeninas
(74) *Attorney, Agent, or Firm* — TraskBritt

(57) ABSTRACT

A method for calibrating a piece of MRI tomography equipment involves constructing a pair of phantoms comprising a physical phantom and a digital twin phantom, determining the virtual image of the digital phantom on the basis of the characteristics of the piece of MRI equipment to be tested, carrying out an MRI sequence with the physical phantom, and verifying the virtual and real image, wherein the digital phantom is produced by solving Bloch equations applied to the characteristics of the physical phantom as a function of the characteristics of the reference sequence.

4 Claims, 7 Drawing Sheets

(56) References Cited

OTHER PUBLICATIONS

[Online] "YALES2BIO", IMAG, Accessed Jun. 2, 2023, (Available at https://imag.umontpellier.fr/~yales2bio/index.html), 1 page.
Brown et al., "Magnetic Resonance Imaging: Physical Principles and Sequence Design", (available at https://onlinelibrary.wiley.com/doi/epdf/10.1002/9781118633953.fmatter), 1999, 30 pages.
International Search Report for International Application No. PCT/FR2021/052173, mailed Apr. 7, 2022, 3 pages.
International Written Opinion for International Application No. PCT/FR2021/052173, mailed Apr. 7, 2022, 6 pages.
Marshall, Ian, "Computational Simulations and Experimental Studies of 3D Phase-Contrast Imaging of Fluid Flow in Carotid Bifurcation Geometries", Journal of Magnetic Resonance Imaging, vol. 39, 2010, 7 pages.
Puiseux et al., "Reconciling PC-MRI and CFD: an In-Vitro Study", NMR in Biomedicine, Research Article, vol. 32, Issue 5, 2019, 18 pages.
Puiseux, Thomas, "Numerical Simulations for Phase-Contrast Magnetic Resonance Imaging", General Mathematics, Universite Montpellier, 2019, 227 pages.
Fortin et al., "Flow MRI simulation in complex 3D geometries: Application to the cerebral venous network" Magnetic Resonance in Medicine, vol. 80, No. 4, (Feb. 5, 2018), pp. 1655-1665.
French Standard, Magnetic resonance equipment for medical imaging—Part 1: Determination of essential image quality parameters, NF EN IEC 62464-1, (Mar. 2019), 94 pages.
Litov, Mark, Creation of a Flow Phantom for MRI Quality Control, ABIH2012 content training course report, URL: http://www.utc.fr/abih; University of Technology of Compiègne, https://www.utc.fr/tsibh/public/3abih/12/stage/litov/index.html, (2012), 17 pages.

\* cited by examiner

CHARACTERIZATION OF DISTORTIONS IN MAGNETIC RESONANCE IMAGING

CROSS-REFERENCE TO RELATED APPLICATIONS

This application is a national phase entry under 35 U.S.C. § 371 of International Patent Application PCT/FR2021/052173, filed Dec. 1, 2021, designating the United States of America and published as International Patent Publication WO 2022/117957 A1 on Jun. 9, 2022, which claims the benefit under Article 8 of the Patent Cooperation Treaty to French Patent Application Serial No. FR2012544, filed Dec. 2, 2020.

TECHNICAL FIELD

The present disclosure relates to the field of the metrology and calibration of a piece of Magnetic Resonance Imaging (MRI) equipment.

BACKGROUND

MRI is a non-invasive, non-ionizing imaging technique that makes it possible to produce two- or three-dimensional tomographic images of the inside of the human body. By virtue of a wide variety of existing acquisition sequences, MRI offers the possibility of evaluating both the anatomical and functional characteristics of organs, with high levels of contrast between tissues. It is of great use when a very fine analysis is necessary and certain lesions are not visible on standard X-rays, ultrasounds, or the scanner.

The MRI principle is based on the magnetic properties of hydrogen atoms, which are contained, to varying degrees, in all tissues of the human body.

By using powerful magnets, the protons of the hydrogen atoms of the body are stimulated simultaneously, which has the effect of aligning their spin magnetic moments in the direction of the magnetic field produced. The sum of the magnetic moments contained in spin samples, called isochromates, corresponds to the magnetization vector. Once this first step has been completed, the atoms are brought into resonance by making them undergo excitation by a magnetic field (radiofrequency). When the stimulation is stopped, the atoms return energy whose intensity is measured and analyzed. Not all tissues contain the same quantity of hydrogen atoms, and the energy level returned will differ according to the tissue composition. The analysis of these data by computers makes it possible to reconstitute images in two and three dimensions and in the three planes of space.

The MRI apparatus contains gradient coils, placed on three axes of a 3D plane. The electric current that passes through these gradient coils produces a local distortion of the main magnetic field. This distortion is used for spatial encoding of the images. It makes it possible, on each axis of a 3D plane (x, y and z), to locate one point in particular. For this, three gradient coils are used: one to reconstitute each of the three planes of 3D MRI images.

To perform an MRI, the patient is placed in a magnet that emits a permanent magnetic field $B_0$, typically 1.5 T or 3 T. This environment stable to hydrogen nuclei disseminated in the human body, to be found in a state of equilibrium. In order to initiate the resonance phenomenon, the supply of energy is carried out via the emission of another specific magnetic field called Bi, which is a field rotating at the Larmor frequency of the hydrogen nuclei, that is a radiofrequency wave of 128 MHz for 3 Tesla magnets, and of 64 MHz for 1.5 T magnets. All hydrogen nuclei of the patient absorb this energy and are therefore in an excited state. When the application of this magnetic field Bi is stopped, all the hydrogen nuclei dissipate the accumulated energy and gradually return to their state of equilibrium. This is when the image is acquired.

The return to equilibrium of the hydrogen nuclei (also called relaxation) is not instantaneous: It therefore requires time. This relaxation phenomenon is characterized by two time constants—$T_1$ and $T_2$—translating this latency of return to equilibrium. Next, the hydrogen nuclei return at varying speeds to their state of equilibrium depending on the environment (or tissue) in which they are located. This therefore results in a reduction or relative increase in relaxation times $T_1$ and $T_2$.

The excitation is carried out by applying a sequence of repeated pulsed RF signals, with echo times TE and repetition times TR forming a reference pattern.

The relaxation signal is captured by the antennas of the MRI imager, which deliver a digital signal that is the subject of processing to turn it into an image. MRI image reconstruction is based on a multidimensional Fourier transform.

The many instruments and different processing steps necessary for the formation of an image give rise to multiple sources of errors that are generally difficult to characterize. Indeed, the magnetic characteristics of the object (relaxation time, proton density), instrumentation (permanent magnet, gradient coils, radio-frequency antennas), and the acquisition and reconstruction parameters (echo time, spatiotemporal resolution, sampling frequency) are just some of the factors that affect the quality of the MRI signal and may alter the image. In practice, distortions result in variations in the position and intensity of the voxels on the images relative to their actual position.

However, the quality of the MRI image is crucial for the relevance of the diagnosis and use of this information for a therapy, in particular for the diagnosis and precise location of a tumor for therapeutic treatment and for adjusting margins in the context of ablation or radiotherapy. Identifying the factors responsible for image distortions thus represents a way of optimizing the MRI measurement.

The present disclosure relates to the calibration of a piece of MRI tomography equipment, in order to ensure the quality of the MRI images and to overcome the observed degradations due either to the malfunctioning of the equipment itself (machine), or to the limitations of the image reconstruction process or sequence.

It is known from the prior art to use a phantom that makes it possible to verify the image obtained and to compare it with a reference image obtained with a perfectly calibrated piece of MRI equipment. This solution is, for example, described in the memo https://www.utc.fr/tsibh/public/3abih/12/stage/litov/index.html.

The European standard NF EN 62464-1 "Magnetic resonance equipment for medical imaging—Part 1: Determination of essential image quality parameters," which defines protocols for verifying parameters that may influence the quality of MRI images, is also known.

Scientific publications relating to flow simulation algorithms are also known.

The publication "FORTIN ALEXANDRE ET AL: "Flow MRI simulation in complex 3D geometries: Application to the cerebral venous network," MAGNETIC RESONANCE IN MEDICINE, vol. 80, no. 4, 5 Feb. 2018 (2018 Feb. 5), pages 1655-1665, XP055839967" describes an example development of a computing tool for simulating the motion of MRI spin flows to study angiography flow artifacts. It mentions comparing simple flow models with real experiments on a physical flow phantom to verify the relevance of the digital simulation tool.

The purpose of the research described in the article is to provide a versatile tool for the simulation of MRI measurements on fluids and arbitrarily complex flow motion. The method described requires recording a limiting amount of data (the trajectories of all the spins moving over time), which makes the simulations excessively demanding in terms of computing resources.

Another article, MARSHALL IAN: "Computational simulations and experimental studies of 3D phase-contrast imaging of fluid flow in carotid bifurcation geometries," JOURNAL OF MAGNETIC RESONANCE IMAGING, vol. 31, no. 4, 29 Mar. 2010 (2010 Mar. 29), pages 928-934, XP05583940, also relates to the general field of MRI digital simulation for predicting the appearance of physiological flows.

The patent application WO2019211556A1 is also known, which relates to the characterization of the degree of confidence as to the measurements of MRI flows by imaging flows via magnetic resonance imaging (MRI) called "4D flow," by imaging a phantom. It involves carrying out an acquisition of the MRI flow data by phase contrast imaging from a physical phantom supplied with a reference fluid feed sequence, to record a second digital data file measured experimentally, then to carry out steps of resetting, correcting, and shaping of the data, these steps being necessary for spatiotemporal compatibility, before proceeding to compare the digital data files in order to calculate at least one error indicator representative of the differences between the digital files.

The solutions of the prior art do not relate to calibrating a piece of physical equipment intended to acquire 4D MRI images, but rather relate to simulation tools. No MRI device calibration solution is totally satisfactory since they largely depend on the quality of the control image of a phantom made on a piece of reference equipment, which may itself have multiple imperfections. Furthermore, by acquiring an MRI image of such a phantom, it is impossible to determine the origin of any degradations in quality.

BRIEF SUMMARY

The present disclosure aims to overcome the drawbacks of the prior art by a solution for calibrating a piece of MRI equipment consisting, in the most general case of the present disclosure, of constructing a pair of phantoms comprising a physical phantom and a counterpart digital phantom, of determining the virtual image of the digital phantom from the characteristics of the MRI equipment to be tested, of carrying out an MRI sequence with the physical phantom, and of verifying the virtual and real images, the digital phantom is produced by solving Bloch equations applied to the characteristics of the physical phantom as a function of the characteristics of the reference sequence.

Advantageously, the mapping of the virtual isochromates of the digital phantom is computed, and this mapping of the virtual isochromates is compared with the mapping of the isochromates obtained by an MRI tomography of the physical phantom in order to determine the differences.

Optimally, the processing of solving the Bloch equations is carried out "on the fly" without storing the data relating to the trajectories of the particles, in the case of a flow phantom or one driven by a motion. This original feature prevents massive storage of the spatiotemporal trajectories of the spins, unclogging the limits in terms of computing resources.

According to one variant, the step of calculating a mapping of the isochromates by the digital model consists of:
modeling the isochromates with Lagrangian particles deposited within any mesh, using the speed derived from a CFD to update each particle position "on the fly,"
solving the Bloch equations independently for each particle.

General Overview of the Present Disclosure

The present disclosure relates to a method and a system for verifying proper operation of MRI equipment and identifying the sources of errors.

Identifying the sources of errors means that the following types of distortions are differentiated:
object: image artifacts induced by the characteristics of the object to be imaged such as physiological movements (patient movement, breathing, heartbeat) or its material composition (presence of metal devices).
machine: imperfections and limitations of the instrumentation affecting the expected characteristics of the acquisition system. These imperfections include the homogeneity of the permanent magnetic field, the linearity of the magnetic fields produced by the gradient coils, the eddy current effects, or the spatial sensitivity during the reception and emission of the signal by the radiofrequency antennas.
sequence: distortions due to non-optimal operator-dependent acquisitions parameters that affect the quality of the image (echo time, encoding rate, sampling frequency). Indeed, the appliance manufacturers generally offer clinical protocols equipped with pre-established sequence parameters as a function of the type of imaging to be carried out. These sequences can be adapted directly on-site, or by the application engineer during software updates. It is therefore possible to see poorly calibrated or obsolete protocols still being used in practice.

Limitations intrinsic in the sequence (imperfect character of the "spoilers," speed encoding) demonstrating the ability of an acquisition to measure the physical reality are also sequence limitations.

image reconstruction: artifacts related to discrete truncation and sampling effects of Fourier space.

Identifying the Sources of Errors Entails a System Consisting of:

A (morphological or functional) physical phantom whose image obtained by the MRI equipment to be characterized is intended for comparison with an image digitally calculated from:
the operating parameters of the MRI equipment to be characterized,
the virtual configuration of the physical phantom,
and optionally disruptive parameters.

A computer program for calculating a digital twin of the aforementioned physical phantom, based on the principle of the numerical solution of the Bloch equations. These equations govern the movement of the nuclear magnetization subjected to a magnetic field and are central to the image formation process. This computer application is referred to as "synthetic MRI."

The method proposed by the present disclosure does use the modeling of the Bloch equations, but does not record the spin trajectories. The method that is the subject of the present disclosure solves in real-time ("on the fly") the effect of these movements in terms of magnetization, which eliminates the need to record colossal volumes of data. This method, the only one of its kind, also makes it possible to solve any complex flow in the MRI field, without being limited by the computing resources.

MRI images of a physical phantom whose characteristics are perfectly controlled and known are acquired with an MRI sequence to be characterized.

The evolution of the magnetization within the same virtualized phantom subjected to this same sequence is numerically solved with the computer program, by virtue of the synthetic MRI program. The advantage of the simulation here is to be able to reconstruct a virtual image corresponding to a given MRI sequence, but free from any error specific to the experimental measurement.

The comparison between the experimentally acquired image (experimental image) and the virtual image obtained by synthetic MRI makes it possible to highlight any imperfections in the instrumentation system (machine malfunctions).

The use of an experimental phantom whose anatomical and/or functional characteristics are known makes it possible to eliminate the image distortions induced by the characteristics of the aforementioned object.

In order to identify the errors related to the sequence and to the acquisition parameters, a third image called a "reference image" is designed from the known geometry of the MRI phantom (virtual phantom) and from the sequence. To ensure a spatial match with the MRI image, the geometry of the virtual phantom is resampled on a voxel image, of the same size and spatial resolution as the acquisition matrix. In the case of Cartesian filling of k-space, the effects of truncation and sampling of the Fourier space are also taken into account by applying spatial filtering as defined in (Haacke, M. E., R. W. Brown, M. R. Thompson and R. Venkatesan Magnetic Resonance Imaging: Physical Principles and Sequence Design. Wiley-Liss. Haacke, 1999) during the resampling process of the virtual phantom. The errors associated with the reconstruction of the image can be estimated by comparing the reference image with and without the application of this filtering. In the case of a non-Cartesian filling of k-space, these effects are taken into account by applying a Fourier transform to the resampled image in order to design a reference k-space.

The residual distortions observed by comparing the reference image to the virtual image obtained by simulated MRI are therefore the consequence of errors induced by the sequence.

BRIEF DESCRIPTION OF THE DRAWINGS

Other features and advantages of the present disclosure will become apparent on reading the following detailed exemplary embodiments, with reference to the accompanying figures, which respectively show.

DETAILED DESCRIPTION

The present disclosure relates to the field of metrology in general, whereby a reference phantom imaged by magnetic resonance (MRI) is compared to a simulation of a virtual MRI apparatus characterized by the true MRI sequence played by the imaging system during acquisition. The method thus makes it possible to determine the origin of the differences observed between reference and simulation. It may be a poor design of the MRI sequence, or in the opposite case, a so-called "machine" problem, which instead involves a failure of an electronic, mechanical or electromagnetic response.

The purpose of calibrating equipment is to compensate for the gain disparities of detectors based on avalanche photodiodes (APDs) which generate inter-channel differences, in particular, to compensate for magnetic field heterogeneities, to compensate for the rise time defects of the switched gradients and more generally to verify the origin of degradations observed either due to malfunctioning of the equipment itself (machine), or due to the limitations of the sequence or of the image reconstruction process.

Figure 1:
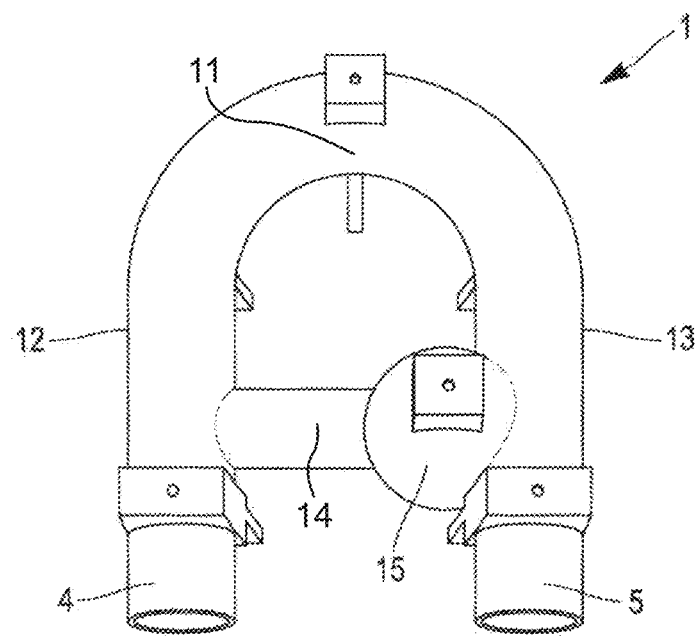
FIG. 1 shows a perspective view of an example 4D flow MRI phantom for the implementation of the present disclosure designed by 3D printing, and used to evaluate the 4D flow MRI sequences.
Figure 2:
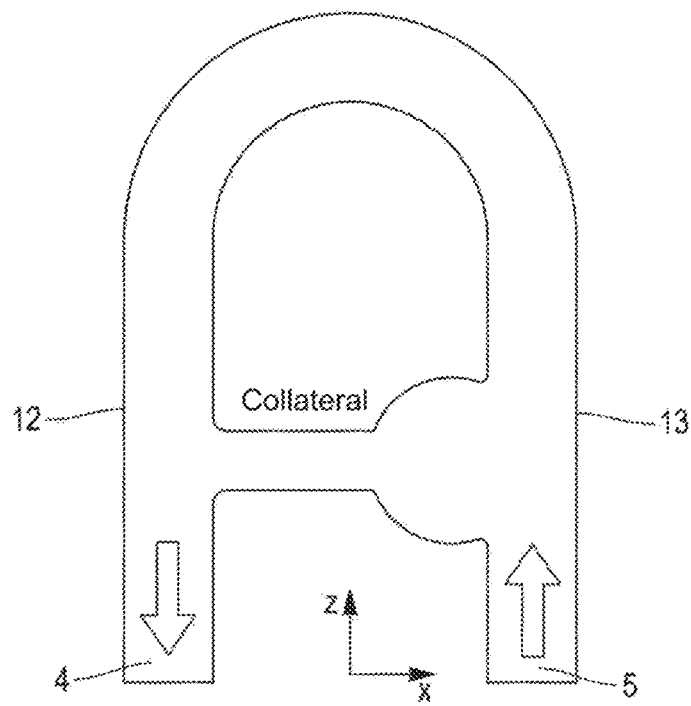
FIG. 2 shows a cross sectional view of the MRI phantom along the median plane of the axis XZ.
Figure 3:
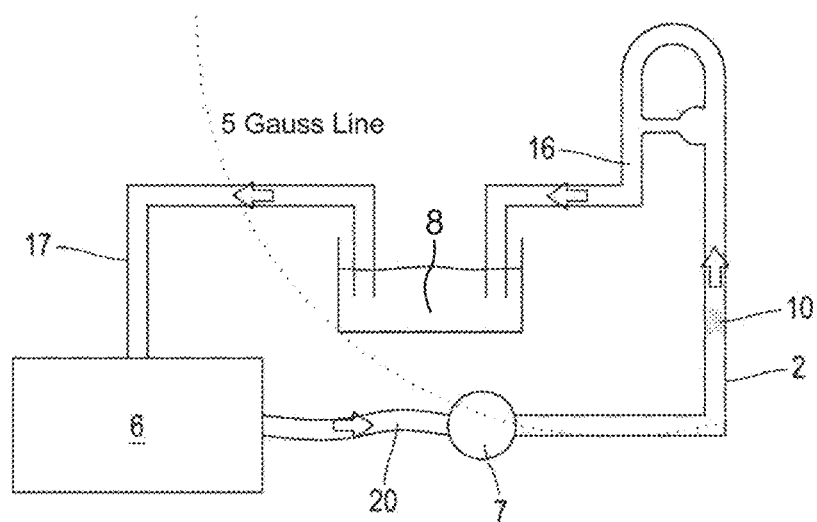
FIG. 3 shows a schematic view of the test bench.

Unlike the documents of the prior art, this does not involve developing a computer tool for simulation of the movement of the spin flows in MRI for the study of angiography flow artifacts for modeling, but rather adjusting an operational item of functional exploration equipment.
Description of an Example Embodiment FIG. 1 shows an example of a geometric configuration of a flow phantom (1), having a general U shape with a curved zone (11) of constant circular cross-section extended on either side by two branches (12, 13). These two branches (12, 13) are connected by a transverse duct (14) with an inlet hemispherical volume (15) simulating an aneurysm. The branches of the U (12, 13) have an inlet connector (5) and an outlet connector (4).

The phantom (1) is connected to a rigid inlet tube (2) for supplying a pulsed fluid coming from a pump (6) and by an outlet rigid tube (16). The length of these tubes (2, 16) is typically 80 centimeters, with a cross-section of 26 millimeters. They are connected to the pump (6) by flexible pipes (17, 20) via connectors. The feed tube (2) comprises a "honeycomb" flow stabilizer (10) that has the effect of laminating the flow entering the phantom (1) by reducing its vortex movement. It also comprises a purge tap and a valve. A flow meter (7) is placed in series to control the instantaneous flow feeding the phantom (1). The phantom has openings where pressure sensors are connected. The shape is chosen to generate a complex, realistic flow, such as that observed in the large circulation (aorta-heart) of the cardiovascular system.

The inner diameter of the phantom (1) is 26 mm and has been designed with a radius of curvature of 50 mm to mimic the blood flows of the aortic arch.

A collateral branch (14) has been established by analogy with the collateral arteries. The size of this collateral branch was designed to reproduce the resolution observed in vivo between the aorta and the supra-aortic trunk, celiac, renal and iliac arteries.

Finally, the protuberance (15) attached to the intersection between the collateral branch (14) and the main branch (13) simulates the blood flows in aortic aneurysms, but also makes it possible to assess the vortices present in the heart chambers.

The shape of the phantom is first made numerically with computer-aided design software. The CAD file then constitutes the digital base to prepare, on the one hand, a hemodynamic digital phantom and, on the other hand, the physical phantom, by a 3D-printing technique based on stereolithography.

The physical phantom is placed in the MRI equipment, in place of the patient, after having been placed in a pouch filled with a gel. It is supplied by a circuit comprising a pump (6) and a flow meter (7) as well as a buffer tank (8). The pump (6) is computer-controlled to provide reproducible waveforms. The fluid has hydrodynamic characteristics that are close to those of blood in general circulation, viscosity=4 cPoi and density=1020 kg/m 3 and the known longitudinal and transverse relaxation times at 1.5 T (T1=0.85 and T2=0.17).

The pump delivers a pulsed flow rate that is controlled at all times by the flow meter (7). The pressure sensors make it possible to validate the hydrostatic pressure maps reconstructed from the velocity maps.

From a clinical point of view, it is particularly advantageous to characterize measurement errors for 4D flow MRI sequences in order to best quantify the reliability and accuracy of the reconstructed hemodynamic markers by virtue of this technique. This methodology applied to 4D flow MRI therefore makes it possible to evaluate the ability of a clinical protocol to quantify a flow.

To expand on this example, it is necessary to consider the following two pre-existing elements:

An experimental test bench equipped with an MRI phantom (1) in which a physiological pulsatile flow is known by virtue of the numerical simulation of the Navier-Stokes equations (Computational Fluid Dynamics—CFD). Several comparisons with idealized MRI measurements made it possible to validate the simulations and the flow within the MRI phantom (1). The steps and results of this validation are detailed in (Puiseux T, Sewonu A, Meyrignac O, et al. Reconciling PC-MRI and CFD: an in vitro study. NMR in Biomedicine. 2019). This numerical flow is referred to hereinafter as a "reference flow."

A method for digitally simulating the magnetization process taking place in MRI during a 4D Flow measurement developed in the software YALES2BIO (https://image.umontpellier.frt~yales2bio/index.html), and a proof of concept, documentation and several validation cases of which are available. The software includes a method for numerically solving the equations that govern the movement of the nuclear magnetization subjected to a magnetic field (Bloch equations). This program is referred to hereinafter as "synthetic MRI."

Implementation of the Present Disclosure

Figure 9:
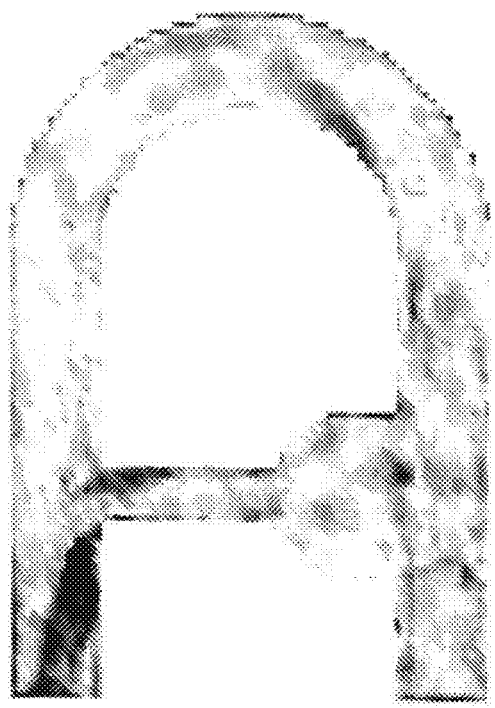
FIG. 9 shows a view of the error calculated between MRI-CFD at the systolic peak.
Figure 10:
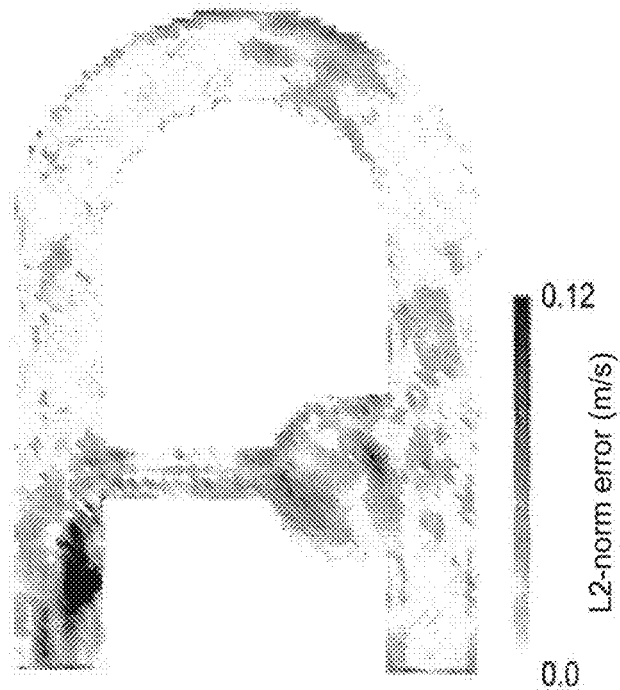
FIG. 10 shows a view of the error calculated between SMRI-CFD at the systolic peak.
Figure 11:
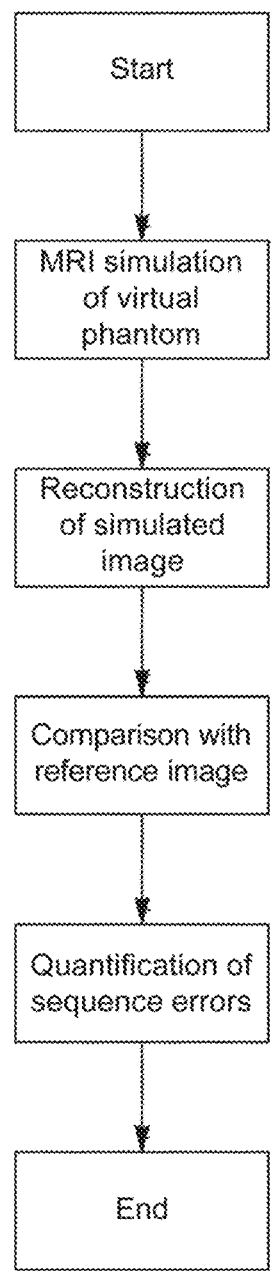
FIG. 11 shows a schematic view of the process of characterizing sequence errors.
Figure 12:
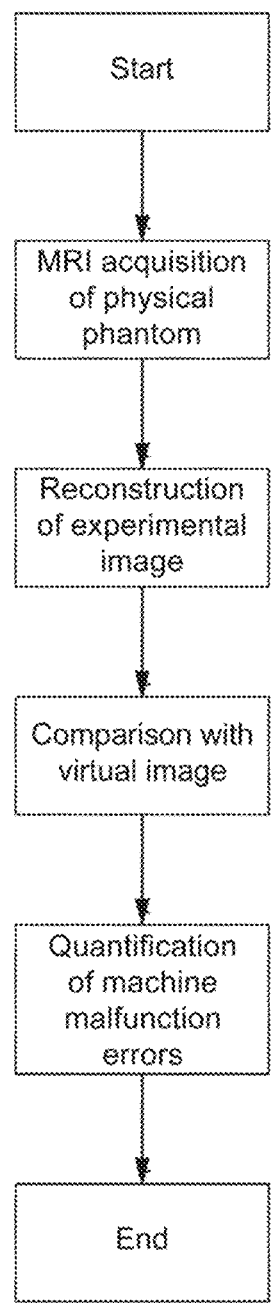
FIG. 12 shows a schematic view of the process of characterizing machine malfunctions.

The implementation of the present disclosure is broken down into two steps:
the first part of the errors specific to the sequence and to the image reconstructor are identified (FIGS. 4 to 6).
the second part is devoted to identifying machine malfunctions (FIGS. 9 and 10).

Sequence-Related Error Identification

This first step consists of simulating the 4D flow MRI sequence from the reference flow in order to reconstruct the image and thus the velocity field that should be obtained by an ideal acquisition (without experimental errors).

To simulate the acquisition of a 4D flow MRI sequence, the volume of the MRI phantom (1) is discretized into a digital mesh consisting of tetrahedral elements. The Bloch equations are numerically solved on Lagrangian particles deposited periodically at each repetition time within the fluid domain, and simultaneously moved by following the solution of the Navier-Stokes equations. The magnetic field that appears in the Bloch equations is represented by the MRI sequence in question and is updated at each iteration. The MRI signals resulting from the relaxation properties of the particles encoded in space and speed are collected sequentially during the application of the reading gradients, and stored in a Fourier space. The periodic pulsed flow imposed by the pump is divided into several time phases, and a virtual image is reconstructed by 3D inverse Fourier transform for each of these phases. Finally, each image reconstructed by the MRI simulation is compared to the reference image corresponding to the same phase.

To construct a reference image compatible with an image obtained by MRI, the reference flow is degraded in space and in time. In order to reproduce the effect by sequential filling of the k-space, the solutions obtained by CFD over time are previously averaged in phase over a duration of 40 time periods.

The phase-averaged numerical solution is then resampled on a Cartesian grid of the same size and resolution as the simulated image. To do this, at each node of the mesh a spatial filtering is applied that takes into account the discrete truncation and sampling effects of the Fourier space, thus making it possible to reproduce the errors related to the image reconstruction process.

The differences observed between the velocity field reconstructed by MRI simulation and the resampled reference flow on the voxel grid (see FIG. 4) then correspond to distortions caused purely by the limitations of the MRI sequence and its acquisition parameters. For this case study, a maximum error is observed that is approximately equal to 20% of the encoding rate.

It is sometimes possible to more deeply characterize these errors by a finer analysis of the characteristics of the sequence.

Figure 4:
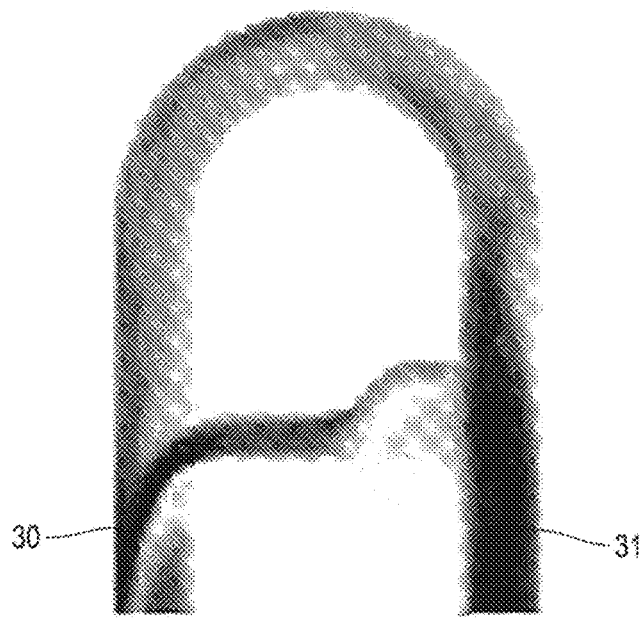
FIG. 4 shows a cross sectional view (see FIG. 1) of the velocity field norm obtained by MRI simulation (uSMRI), at the systolic peak.
Figure 5:
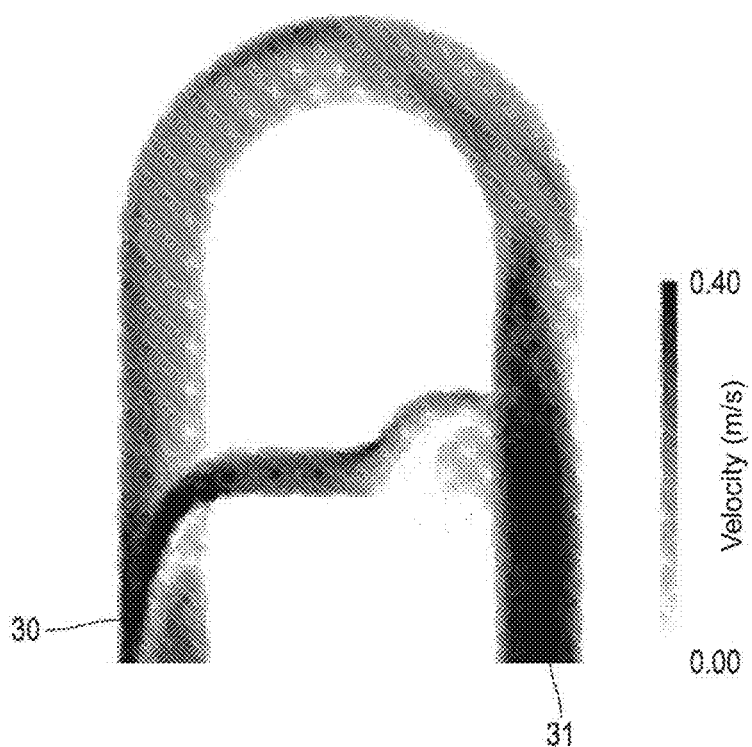
FIG. 5 shows a cross sectional view of the velocity field norm obtained by CFD simulation (uCFD), at the systolic peak.
Figure 6:
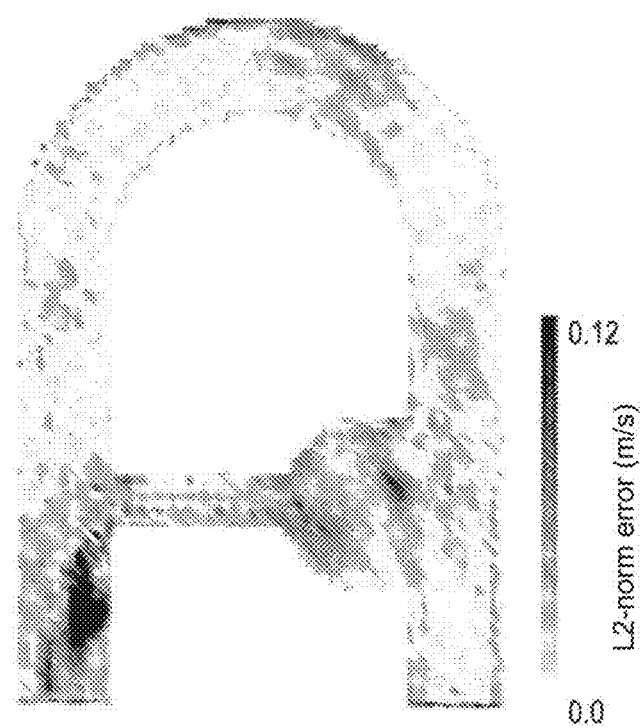
FIG. 6 shows a view of the error defined as ‖uSMRI−uvox‖ where uvox corresponds to the CFD field resampled on the voxel grid.

FIGS. 4 to 6 show the standard of the velocity field obtained at the systolic peak by MRI simulation (uSMRI) (FIG. 4) and by CFD (uCFD) (FIG. 5) as well as the error defined as $\|uSMRI-uvox\|$ where uvox corresponds to the CFD field and resampled on the voxel grid (FIG. 6).

Figure 7:
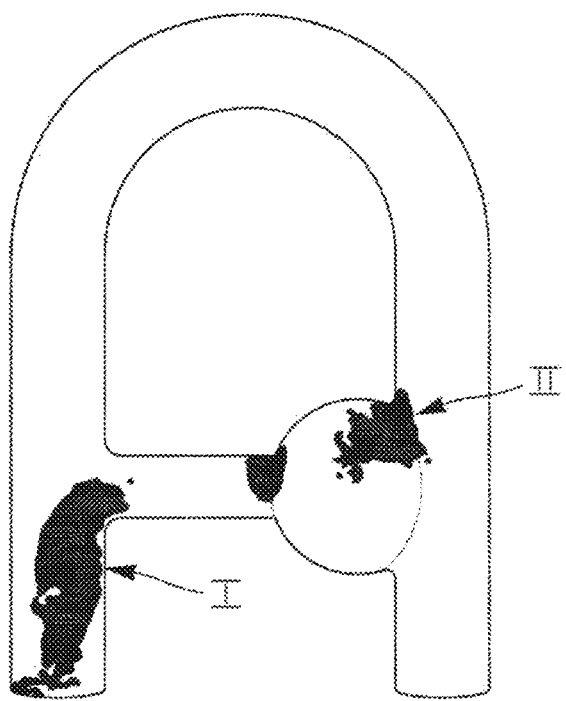
FIG. 7 shows a 3D view of the higher-acceleration CFD regions at the systolic peak.
Figure 8:
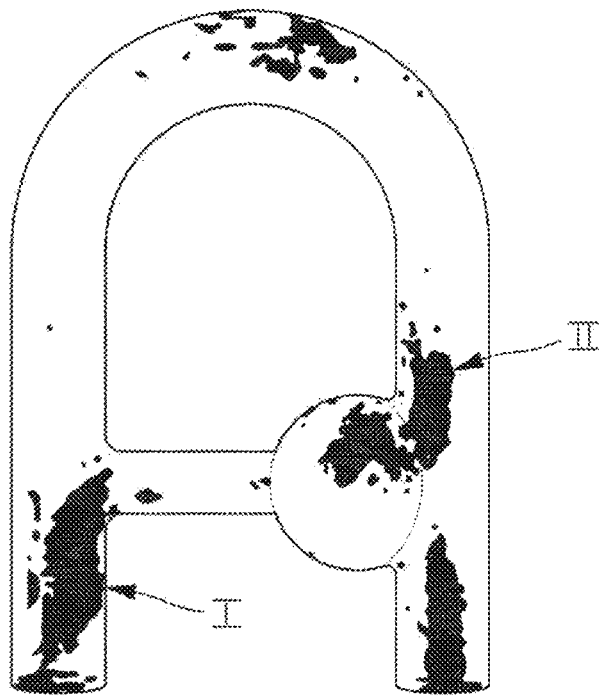
FIG. 8 shows a view of the corresponding CFD-SMRI error.

FIG. 7 shows the spatial structures of greater acceleration in the reference flow. FIG. 8 shows the largest velocity errors in the synthetic MRI at the corresponding time. The similarities observed between these two quantities suggest the presence of an acceleration artifact. Indeed, a hypothesis inherent to the 4D flow MRI sequences is that there is a linear relationship between the phase and the position of a nuclear spin. In other words, the effects induced by the acceleration of the spins are ignored in the sequences of 4D flows.

This first step makes it possible to quantify the level of error introduced by certain approximations of the sequence. By characterizing the observed image artifacts, this methodology may also be extended to the optimization of MRI sequences.

Identifying Machine Malfunctions

Insofar as the reference flow is similar to the experimental flow within the MRI phantom, the comparison between the images acquired experimentally and those simulated by means of the same 4D flow MRI sequence enables the identification of possible malfunctions of the instrumentation system.

The experimentally reconstructed images are compared with the images obtained by MRI simulation. The differences observed between the two velocity fields indicate machine errors. The velocities reconstructed by experimental and synthetic MRI are compared with the reference image in FIGS. 9 and 10. Similar error structures can be distinguished, showing that experimental MRI clearly reproduces the acceleration artifact discussed in the preceding part. It is also possible to note a systematically higher error level of experimental MRI, suggesting the presence of distortions due to the instrumentation. The evaluation of the operation of the instrumentation system does not require a complex sequence to be acquired. In fact, single MRI sequences composed of elementary magnetic pulses are theoretically sufficient to warn of any malfunctions. For example, this can make it possible to separately test the different magnetic field gradient coils.

The invention claimed is:

1. A method for calibrating a piece of MRI tomography equipment to compensate for degradations in quality of images provided by the equipment to be calibrated and caused by malfunction of the equipment to be calibrated, MRI sequence limitations or image artifacts, the method comprising a step of determining an origin of the degradations in the quality of the images, the step comprising:
   constructing a pair of phantoms comprising a physical phantom and a digital twin phantom;
   determining a virtual image of the digital twin phantom on a basis of the characteristics of a piece of MRI equipment to be tested;
   carrying out an MRI sequence with the physical phantom; and
   verifying the virtual and a real image, wherein the digital twin phantom is produced by solving Bloch equations on-the-fly, without recording spin trajectories, applied to the characteristics of the physical phantom as a function of the characteristics of the reference sequence.

2. The method of claim 1, further comprising computationally mapping of virtual isochromates of the digital twin phantom, and comparing the mapping of the virtual isochromates with mapping of the virtual isochromates obtained by an MRI tomography of the physical phantom to determine the differences.

3. The method of claim 2, wherein the computational mapping of the virtual isochromates of the digital twin phantom comprises:
   modeling the virtual isochromates with Lagrangian particles deposited within any mesh, using a speed derived from a CFD to update each particle position on the fly; and
   solving the Bloch equations independently for each particle.

4. A method for calibrating a piece of MRI tomography equipment to compensate for degradations in quality of images provided by the equipment to be calibrated and caused by malfunction of the equipment to be calibrated, MRI sequence limitations or image artifacts, the method comprising a step of determining an origin of the degradations in the quality of the images, the step comprising:
   constructing a pair of phantoms comprising a physical phantom and a digital twin phantom;
   acquiring a real image of the physical phantom using an MRI sequence on the piece of MRI tomography equipment to be calibrated;
   generating a virtual image of the digital twin phantom on a basis of the characteristics of the piece of MRI equipment to be calibrated by solving Bloch equations on-the-fly, without recording spin trajectories, applied to the characteristics of the physical phantom as a function of the characteristics of the MRI sequence;
   comparing the virtual image generated and the real image acquired to identify and characterize errors linked to the malfunctions of the equipment to be calibrated, to the MRI sequence limitations or to the image artifacts based on the differences observed between the virtual image and the real image.

* * * * *